US011433202B2

(12) United States Patent
Romano et al.

(10) Patent No.: US 11,433,202 B2
(45) Date of Patent: Sep. 6, 2022

(54) INTERACTIVE GUIDANCE RELATED TO A SUBJECT'S EXPIRATORY FLOW LIMITATION RESULTS

(71) Applicant: KONINKLIJKE PHILIPS N.V., Eindhoven (NL)

(72) Inventors: Robert Romano, Pittsburgh, PA (US); Richard James Mckenzie, Jr., Butler, PA (US)

(73) Assignee: Koninklijke Philips N.V., Eindhoven (NL)

( * ) Notice: Subject to any disclaimer, the term of this patent is extended or adjusted under 35 U.S.C. 154(b) by 945 days.

(21) Appl. No.: 16/211,066

(22) Filed: Dec. 5, 2018

(65) Prior Publication Data

US 2019/0184118 A1   Jun. 20, 2019

Related U.S. Application Data

(60) Provisional application No. 62/599,872, filed on Dec. 18, 2017.

(51) Int. Cl.
*A61M 16/00* (2006.01)
*A61B 5/087* (2006.01)
(Continued)

(52) U.S. Cl.
CPC ............ *A61M 16/024* (2017.08); *A61B 5/085* (2013.01); *A61B 5/087* (2013.01); *A61B 5/742* (2013.01);
(Continued)

(58) Field of Classification Search
CPC ............ A61M 16/024; A61M 16/0003; A61M 2016/0036; A61M 2205/3334;
(Continued)

(56) References Cited

U.S. PATENT DOCUMENTS 4,495,944 A * 1/1985 Brisson ............... A61B 5/087
128/200.23
5,881,723 A * 3/1999 Wallace ............... G16H 40/63
128/204.21
(Continued)

FOREIGN PATENT DOCUMENTS

EP        2253268 A1    11/2010
EP        2668900 A1    12/2013
(Continued)

OTHER PUBLICATIONS

Crayford, Tim et al Mastering Public Health: A postgraduate guide to examinations and revalidation: A Guide to Examinations and Revalidation(MFPH), ISBN 10: 1853157813, 2008 (Absract Only).
(Continued)

*Primary Examiner* — Tu A Vo
(74) *Attorney, Agent, or Firm* — Daniel H. Brean; Andrew M. Gabriel (57) ABSTRACT

In certain embodiments, a ventilator may provide interactive guidance for obtaining a subject's expiratory flow limitation results. In some embodiments, the ventilator may cause a progressive color component to be presented, where the progressive color component indicates a progression from one color proximate one side of the progressive color component to another color proximate another side of the progressive color component. The ventilator may cause a forced oscillation to be continuously applied to an airway of the subject for a time period. The ventilator may monitor the subject's degree of expiratory flow limitation based on output signals generated by one or more sensors as the forced oscillation is continuously applied for the time period. The ventilator may cause, based on the monitoring, a movable component's position on the progressive color
(Continued)

component to be continuously updated during the time period to indicate the degree of expiratory flow limitation.

14 Claims, 5 Drawing Sheets

(51) Int. Cl.
*A61B 5/085* (2006.01)
*A61B 5/00* (2006.01)

(52) U.S. Cl.
CPC ..... *A61M 16/0003* (2014.02); *A61M 16/0051* (2013.01); *A61M 2016/003* (2013.01); *A61M 2016/0018* (2013.01); *A61M 2016/0027* (2013.01); *A61M 2016/0036* (2013.01); *A61M 2205/3334* (2013.01); *A61M 2205/502* (2013.01); *A61M 2205/584* (2013.01)

(58) Field of Classification Search
CPC ...... A61M 2205/502; A61M 2205/584; A61B 5/085; A61B 5/087; A61B 5/742
See application file for complete search history.

(56) References Cited

U.S. PATENT DOCUMENTS

| | | | |
|---|---|---|---|
| 6,588,422 B1 * | 7/2003 | Berthon-Jones | A61M 16/00 128/204.23 |
| 6,915,803 B2 * | 7/2005 | Berthon-Jones | A61M 16/00 128/204.23 |
| 7,270,128 B2 * | 9/2007 | Berthon-Jones | A61M 16/024 128/204.23 |
| 9,649,050 B2 * | 5/2017 | Van Den Aardweg | A61B 5/085 |
| 2003/0213491 A1 * | 11/2003 | Berthon-Jones | A61M 16/0069 128/204.21 |
| 2005/0005938 A1 * | 1/2005 | Berthon-Jones | A61M 16/00 128/204.22 |
| 2006/0032503 A1 * | 2/2006 | Berthon-Jones | A61M 16/00 128/204.23 |
| 2007/0185406 A1 * | 8/2007 | Goldman | A61B 5/08 600/533 |
| 2008/0039735 A1 | 2/2008 | Hickerson | |
| 2008/0221495 A1 | 9/2008 | Steffens | |
| 2010/0147305 A1 * | 6/2010 | Dellaca' | A61B 5/085 600/533 |
| 2010/0275921 A1 * | 11/2010 | Schindhelm | G16H 40/67 600/533 |
| 2012/0192867 A1 * | 8/2012 | Lewis | A61M 16/0051 128/204.21 |
| 2015/0011906 A1 * | 1/2015 | Wallach | A61B 5/7455 600/538 |
| 2015/0193585 A1 * | 7/2015 | Sunna | G06F 3/04883 345/173 |
| 2015/0283342 A1 * | 10/2015 | Mielcarz | A61M 16/0051 128/202.22 |
| 2015/0320955 A1 * | 11/2015 | Mahadevan, Jr. | A61M 16/0003 128/204.23 |
| 2016/0256642 A1 * | 9/2016 | Soysa | A61M 16/16 |
| 2018/0160970 A1 * | 6/2018 | Khoury | A61M 16/024 |

FOREIGN PATENT DOCUMENTS

| | | | | |
|---|---|---|---|---|
| WO | 2013070712 A1 | 5/2013 | | |
| WO | WO2013163740 A1 | 11/2013 | | |
| WO | WO-2016079703 A1 * | 5/2016 | ......... | C07D 405/14 |
| WO | WO2016079703 A1 | 5/2016 | | |
| WO | WO2017136639 A1 | 8/2017 | | |

OTHER PUBLICATIONS

PCT International Search Report, International application No. PCT/EP2016/084076, dated Apr. 15, 2019.

* cited by examiner

```
┌─────────────────────────────────────────────────────────────┐
│ Cause a progressive color component to be presented on a    │
│ user interface                                               │
│                          302                                 │
└─────────────────────────────────────────────────────────────┘
                              │
                              ▼
┌─────────────────────────────────────────────────────────────┐
│ Cause a forced oscillation to be continuous applied to an    │
│ airway of the subject for a time period                      │
│                          304                                 │
└─────────────────────────────────────────────────────────────┘
                              │
                              ▼
┌─────────────────────────────────────────────────────────────┐
│ Monitor, during the time period, the subject's degree of     │
│ expiratory flow limitation based output signals generated    │
│ by one or more sensors as the forced oscillation is          │
│ continuous applied for the time period                       │
│                          306                                 │
└─────────────────────────────────────────────────────────────┘
                              │
                              ▼
┌─────────────────────────────────────────────────────────────┐
│ Cause, based on the monitoring, a movable graphical          │
│ component's position on the progressive color component      │
│ to be continuously updated during the time period to         │
│ indicate the degree of expiratory flow limitation            │
│                          308                                 │
└─────────────────────────────────────────────────────────────┘
```

INTERACTIVE GUIDANCE RELATED TO A SUBJECT'S EXPIRATORY FLOW LIMITATION RESULTS

CROSS-REFERENCE TO RELATED APPLICATIONS

This patent application claims the priority benefit under 35 U.S.C. § 119(e) of U.S. Provisional Application No. 62/599,872, filed on Dec. 18, 2017, the contents of which are herein incorporated by reference.

BACKGROUND OF THE INVENTION

1. Field of the Invention

The present disclosure pertains to providing guidance related to a subject's respiratory test results, including, for example, providing interactive guidance related to a subject's expiratory flow limitation results.

2. Description of the Related Art

Clinicians often rely on respiratory diagnostic systems to determine optimal therapy or treatment options. Some respiratory diagnostic systems can determine expiratory flow limitation, dynamic hyperinflation, or other respiratory information. Although typical respiratory diagnostic systems display various real-time waveforms corresponding to respiratory measurements, respiratory diagnostic systems generally lack more user-friendly guidance during or subsequent to performance of a respiratory test with regard to the test or results thereof. These and other drawbacks exist.

SUMMARY OF THE INVENTION

Accordingly, one or more aspects of the present disclosure relate to a ventilator configured to providing interactive guidance related to a subject's expiratory flow limitation results, the ventilator comprising: one or more sensors configured to be placed at or near a subject's mouth and to generate output signals conveying information related to the subject's inspiration or expiration of gas; and one or more physical processors configured by machine readable instructions to: cause a progressive color component to be presented on a user interface, the progressive color component indicating a progression from one color proximate one side of the progressive color component to another color proximate another side of the progressive color component; cause, via an oscillator, a forced oscillation to be continuously applied to an airway of the subject for a time period; monitor, during the time period, the subject's degree of expiratory flow limitation based on the sensor-generated output signals as the forced oscillation is continuously applied for the time period; and cause, based on the monitoring, a movable graphical component's position on the progressive color component to be continuously updated during the time period to indicate the subject's degree of expiratory flow limitation.

Another aspect of the present disclosure relates to a method of providing interactive guidance related to a subject's expiratory flow limitation results, the method being implemented by a computer system comprising one or more physical processors configured by machine readable instructions to perform the method, the method comprising: causing a progressive color component to be presented on a user interface, the progressive color component indicating a progression from one color proximate one side of the progressive color component to another color proximate another side of the progressive color component; causing a forced oscillation to be continuously applied to an airway of the subject for a time period; monitoring, during the time period, the subject's degree of expiratory flow limitation based output signals generated by one or more sensors as the forced oscillation is continuously applied for the time period; and causing, based on the monitoring, a movable graphical component's position on the progressive color component to be continuously updated during the time period to indicate the subject's degree of expiratory flow limitation.

Still another aspect of present disclosure relates to a system for providing interactive guidance related to a subject's expiratory flow limitation results, the system comprising: means for causing a progressive color component to be presented on a user interface, the progressive color component indicating a progression from one color proximate one side of the progressive color component to another color proximate another side of the progressive color component; means for causing a forced oscillation to be continuously applied to an airway of the subject for a time period; means for monitoring, during the time period, the subject's degree of expiratory flow limitation based output signals generated by one or more sensors as the forced oscillation is continuously applied for the time period; and means for causing, based on the monitoring, a movable graphical component's position on the progressive color component to be continuously updated during the time period to indicate the subject's degree of expiratory flow limitation.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
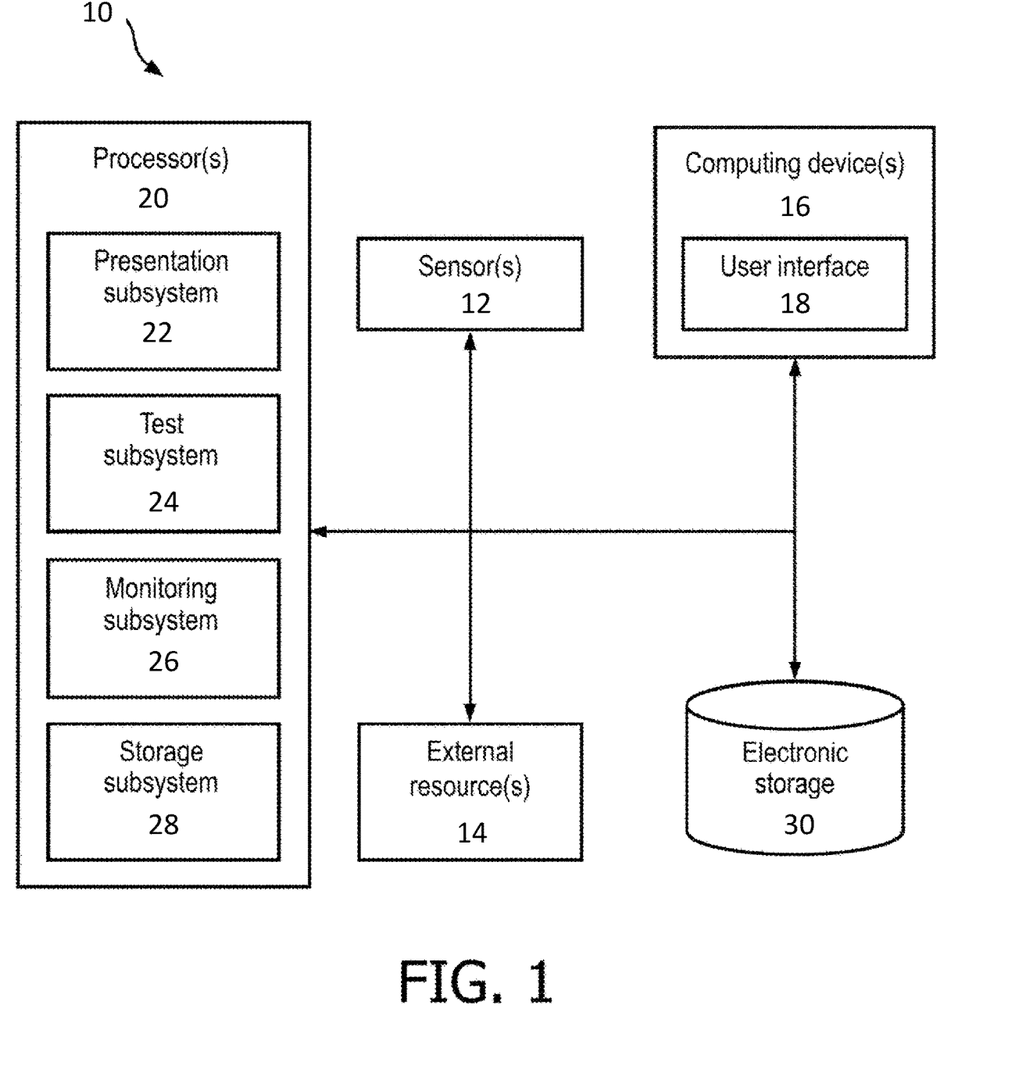
FIG. 1 illustrates a system configured to facilitate a subject's respiratory test and/or guidance related to the respiratory test, in accordance with one or more embodiments.

FIG. 1 illustrates system 10 configured to facilitate a subject's respiratory test and/or guidance related to the respiratory test, in accordance with one or more embodiments. In some embodiments, system 10 may monitor respiratory information (or other information) associated with a patient during one or more time periods and update one or more components on a user interface based on such information. As an example, system 10 may continuously monitor such information during a time period (e.g., a time period of a test or other time period) derived from output signals generated from one or more sensors (e.g., sensors 12). As new information is determined, such information may be utilized to update one or more components on the user interface. In one use case, for instance, one or more components of the user interface may be periodically updated during the time period based on new respiratory information as such respiratory information is determined.

In some embodiments, system 10 may present a progressive color component on a user interface, and, based on monitoring of a subject (or information related to the subject) during a time period, system 10 may cause another component's position on the progressive color component to be updated during the time period to indicate the subject's respiratory information (or other information). As an example, the progressive color component may indicate a progression from one color proximate one side of the progressive color component to another color proximate another side of the progressive color component. Such "colors" of the progressive color component may include only grayscale values or include one or more values other than grayscale values (in addition to or in lieu of grayscale values).

As another example, the progressive color component may include a choropleth map, a component having a continuous color scheme that is used to apply different shades of the same color (e.g., such that lighter shades match lower data values and darker shades match higher data values), or other component. Additionally, or alternatively, system 10 may cause the progressive color component to be modified to indicate the subject's repository information. As an example, the progressive color component (or portions thereof) may be shifted in one or more directions relative to one or more other components on the user interface (e.g., such that the color indicative of the subject's respiratory condition is centered on the progressive color component or centered on the user interface). As another example, system 10 may cause a zoom-in or zoom-out operation to be performed such that one or more portions of the progressive color component appear larger (e.g., if zoomed in) or smaller (e.g., if zoomed out) from the perspective of a user viewing the user interface (e.g., where the color indicative of the subject's respiratory condition is emphasized, where one or more colors not indicative of the subject's repository condition is de-emphasized, etc.).

In some embodiments, system 10 may present a numerical scale component on the user interface in addition to or in lieu of the progressive color component, and, based on monitoring of the subject (or information related to the subject) during the time period, system 10 may cause another component's position on the numerical scale component to be updated during the time period to indicate the subject's respiratory information (or other information). The numerical scale component may indicate a progression from one number proximate one side of the numerical scale component to another number proximate another side of the numerical scale component. As an example, the numerical scale component may be a component having a continuous numbering scheme (e.g., such that lower numbers match lower data values and higher numbers match higher data values). Additionally, or alternatively, system 10 may cause the numerical scale component to be modified to indicate the subject's repository information. As an example, the numerical scale component (or portions thereof) may be shifted in one or more directions relative to one or more other components on the user interface (e.g., such that the number indicative of the subject's respiratory condition is centered on the numerical scale component or centered on the user interface). As another example, system 10 may cause a zoom-in or zoom-out operation to be performed such that one or more portions of the numerical scale component appear larger (e.g., if zoomed in) or smaller (e.g., if zoomed out) from the perspective of a user viewing the user interface (e.g., where the number indicative of the subject's respiratory condition is emphasized, where one or more numbers not indicative of the subject's repository condition is de-emphasized, etc.).

Figure 2A:
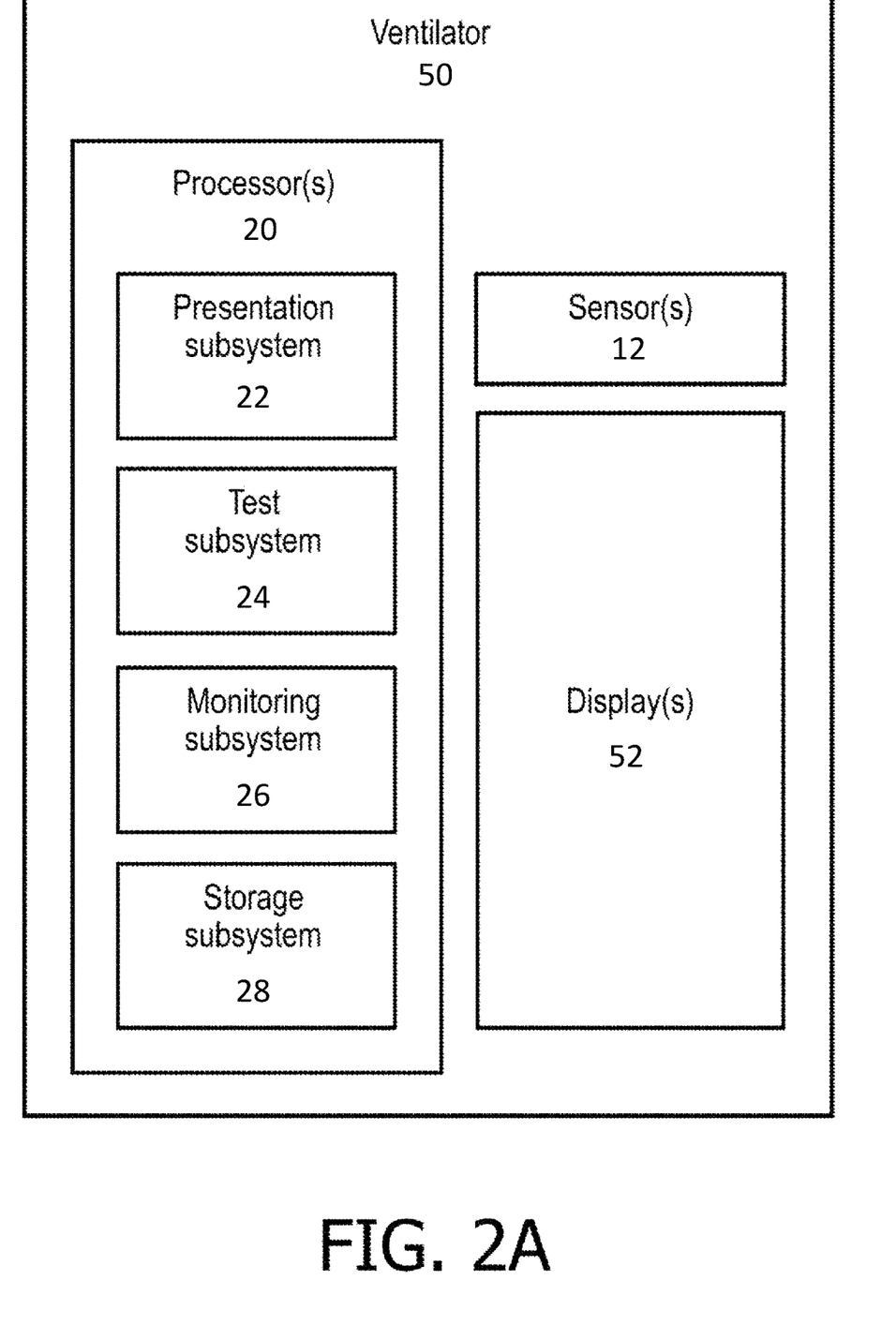
FIG. 2A illustrates a ventilator configured to facilitate a subject's respiratory test and/or guidance related to the respiratory test, in accordance with one or more embodiments.

In some embodiments, with respect to FIG. 2A, ventilator 50 (or ventilator system 50) may include a housing, one or more sensors 12, one or more processors 20, one or more displays 52, or other components. Sensors 12 may include pressure sensors, gas flow sensors, inspiration sensors, expiration sensors, or other sensors. In some embodiments, sensors 12 may be configured to be placed at or near a subject's mouth and to generate output signals conveying information related to the subject's inspiration or expiration of gas. In some embodiments, ventilator 50 may be configured to include one or more sensors 12, one or more processors 20, and one or more displays 52 within the housing. In some embodiments, ventilator 50 may be configured to include one or more sensors 12 and one or more processors 20 within the housing and one or more displays 52 outside of the housing (e.g., attached to the outside of the housing, proximate to but outside of the housing, or otherwise outside of the housing). In some embodiments, ventilator 50 may be configured to include one or more processors 20 and one or more displays 52 within the housing and one or more sensors 12 outside of the housing (e.g., attached to the outside of the housing, proximate to but outside of the housing, or otherwise outside of the housing).

In some embodiments, ventilator 50 may be configured to include one or more processors 20 within the housing and one or more sensors 12 and one or more displays 52 outside of the housing (e.g., attached to the outside of the housing, proximate to but outside of the housing, or otherwise outside of the housing). Sensors 12, processors 20, display 52, and other components of ventilator 50 (e.g., oscillator or other components) whether housed within or outside of the housing may communicate with one another via wired or wireless connections. It should be noted that, although some embodiments are described herein with respect to ventilator 50 performing certain operations, one or more such operations may be performed by one or more other components (e.g., one or more servers, client devices, etc.). As an example, such other components (e.g., one or more servers, client devices, etc.) may include one or more processor components that are the same as or similar to subsystems 22-28.

In some embodiments, ventilator 50 may present a progressive color component on a user interface (e.g., via display 52), where the progressive color component indicates a progression from one color proximate one side of the progressive color component to another color proximate another side of the progressive color component. Ventilator 50 may cause gas to flow from one or more tubes to a mask placed at or proximate a subject's mouth, and ventilator 50 may monitor the subject's inspiration/expiration of gas or other related aspects. As an example, ventilator 50 may cause a forced oscillation (e.g., via an oscillator) to be continuously applied to an airway of the subject for a time period based on the monitoring, ventilator 50 may update one or more components on the user interface (e.g., on a periodic basis or other continuous basis). As discussed, another component's position on the progressive color component may be updated based on the monitoring, or the progressive color component may be modified, to indicate the monitored aspects (e.g., expiratory flow limitation, dynamic hyperinflation, mixture of gases expired by the subject, or other monitored aspects). In this way, for example, the presence of a person's relative degree of expiratory flow limitation or other monitored aspects may be screened and presented on the user interface. As another example, diverging color schemes allow the emphasis of a quantitative data display to show progressions outward from a critical midpoint of the data range. This functionality enables a clinician or other user to make informed decisions about treatment options, including particular treatment via the ventilator or other therapy options for the patient.

Figure 2B:
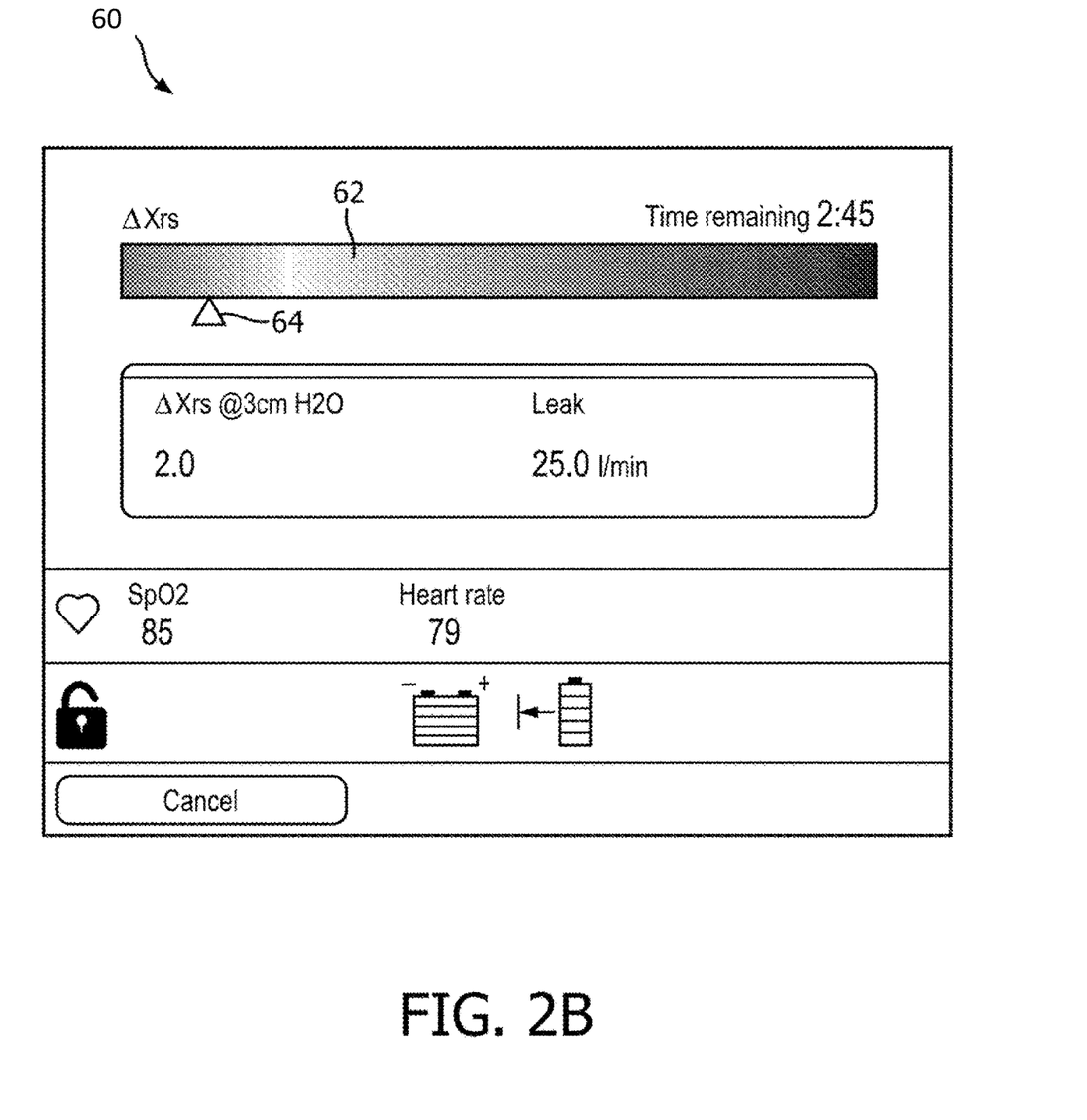
FIG. 2B illustrates a user interface configured to provide interactive guidance related to a subject's expiratory flow limitation results, in accordance with one or more embodiments.

As shown in FIG. 2B, with respect to some use cases, user interface 60 (e.g., on a display 52 of ventilator 50 or other display) may include progressive color component 62 (e.g., having a diverging color scheme) which allow the emphasis of a quantitative data display to have progressions outward from a critical midpoint of the data range that reflects the severity of a person's expiratory flow limitation. Such emphasis may be represented by component 64. In some cases, component 64 may be a moveable graphical component that is continuously updated during a test (or a portion thereof) with respect to its position on progressive color component 62 to indicate the subject's degree of expiratory flow limitation (e.g., the subject's relative degree of expiratory flow limitation). Such moveable graphical component may be continuously updated during the test (or a portion thereof) based on output signals generated by one or more sensors. Additionally, or alternatively, other information may be presented on user interface 60 (e.g., information shown within user interface 60 in FIG. 2B).

In some embodiments, expiratory flow limitation of a subject is determined by detecting via one or more sensors when flow ceases to increase despite increasing expiratory effort. As an example, expiratory flow limitation relates to a physiological condition where a person's airways partially collapse due to a loss of their elastic recoil due to parenchymal destruction or to some other form of airway obstruction. This physiological condition may be detected via one or more forced oscillation techniques. In some embodiments, a ventilator (e.g., ventilator 50) may perform a screening test by applying a fixed pressure (e.g., about 3 cmH2O or other fixed pressure) that will remain constant through the screening session. The screening session results, which will include near real-time pulmonary mechanics information (e.g., including detected expiratory flow limitation or other information), will be kept on a display until the next session is enabled—whether the session was completed or stopped before completion. The screening results will be captured in the ventilator's data storage and transmitted via an electronic interface to external or cloud-based storage or data management system (e.g., over the Internet, over one or more other wired or wireless networks, etc.).

In some embodiments, ventilator 50 may detect a conclusion of a test (e.g., a test of the subject's expiratory flow limitation or other respiratory test), and, based on the detection of the test conclusion, ventilator 50 may modify a pressure of the forced oscillation to a therapeutic pressure for at least a subsequent time period following the conclusion of the test. In some embodiments, one or more components on a user interface may remain fixed until at least an end of the subsequent time period. In one use case, based on the detection of the test conclusion, ventilator 50 may cause a moveable graphical component's position on a progressive color component may be caused to remain fixed until at least an end of the subsequent time period (e.g., although the moveable graphical component's position was periodically changing during performance of the test). In another use case, ventilator 50 may cause aspects of the progressive color component to remain fixed until at least an end of the subsequent time period (e.g., although such aspects were periodically changing during performance of the test as described herein). As an example, the time period for the test may be a fixed time period, and the conclusion of the test may be detected responsive to the occurrence of the end of the fixed time period (e.g., based on a timer or other indication). As another example, the conclusion of the test may be detected responsive to finalization of the subject's degree of expiratory flow limitation. In one use case, the finalization of the subject's degree of expiratory flow limitation may be detected based on one or more degree change thresholds (e.g., if the calculated degree has not changed by more than a first degree threshold for at least a first threshold number of updates or amount of time, if the calculated degree has not changed by more than a second degree threshold value for at least a second threshold number of updates or amount of time, etc.).

As described above, in some embodiments, a ventilator (e.g., ventilator 50) may perform a screening test by applying a fixed pressure (e.g., about 3 cmH2O or other fixed pressure) that will remain constant through the screening session. The screening session results, which will include near real-time pulmonary mechanics information (e.g., including detected expiratory flow limitation or other information), will be kept on a display until the next session is enabled—whether the session was completed or stopped before completion. Moreover, in one use case, when the test concludes (e.g., and the patient is unattended by a clinician), the device will revert from the screening pressure to a therapeutic pressure (e.g., from 3 cmH2O to about 4 cmH2O or other therapeutic pressure, from another screening pressure to another therapeutic pressure, etc.).

In some embodiments, test subsystem 24 may cause a forced oscillation at a fixed frequency (e.g., 5 Hz or other frequency such as 3 Hz, 4 Hz, 6 Hz, 7 Hz, 10 Hz, 20 Hz, or greater or lesser frequency) to be applied to the airways during both the inspiration and expiratory phases of a breath cycle. As an example, the source of the fixed frequency oscillations may include a moving valve, a modulated motor, an adjustment of a blower inlet gap, or other source. In some embodiments, based on output signals generated by one or more sensors (e.g., placed at or near the subject's mouth), monitoring subsystem 26 may continuously measure reactance related to the subject's inspiration of gas during the time period and reactance related to the subject's expiration of gas during the time period as the forced oscillation is continuously applied for the time period. Monitoring subsystem 26 may determine and update the subject's degree of expiratory flow limitation during the time period (e.g., on a periodic basis or other continuous basis) based on differences between the continuous measurements of the reactance related to the subject's inspiration of gas and the continuous measurements of reactance related to the subject's expiration of gas. Such continuous measurements may include performing such measurements on a periodic basis or other continuous basis.

Monitoring subsystem 26 may compute the subject's airway impedance. Monitoring subsystem 26 may further convert the airway impedance into its mathematic real and imaginary components, where the imaginary part is representative of the respiratory system reactance ($X_{rs}$). The difference of the reactance during inspiration to the reactance during expiration, "delta$X_{rs}$", correlates to the degree of expiratory flow limitation. As an example, such algorithm may include averaging the reactance during the expiratory phase of a breath cycle ($X^-e$) minus the average of the reactance during the inspiratory phase of the same breath cycle ($X^-i$), i.e., delta$X_{rs}$=($X^-e$)–($X^-i$). As a further example, based on health information of a subject (e.g., the subject's age, diseases, prior conditions, or other information), an algorithm may be modified to reflect the health information. In one use case, an algorithm derived from actual patient data, that correlates a calculated delta$X_{rs}$ value to one's relative degree of expiratory flow limitation EFLrel may be EFLrel=0.7*delta$X_{rs}$+1.1 or EFLrel α delta$X_{rs}$.

In some embodiments, monitoring subsystem 26 uses the magnitude of this difference (of the reactance during inspiration to the reactance during expiration, "delta$X_{rs}$") to determine the relative degree of expiratory flow limitation, where each "delta$X_{rs}$" value corresponds to a color scheme. That is, a graduated color is used to show a qualitative difference between "delta$X_{rs}$" values. Data is classified into ranges that are each assigned a different color from a color scheme to represent a relative value. As discussed, in some embodiments, presentation subsystem 22 may indicate the relative degree of expiratory flow limitation a choropleth map, a continuous color scheme (e.g., that is used to apply different shades of the same color so that lighter shades match lower data values and darker shades match higher data values), a bi-polar color map (e.g., having two opposite hues to show a change in value from negative to positive or on either side of some either central tendency), or other component on a user interface. In one use case, when mapping temperatures is from dark blue (for cold) to dark red (for hot) with white in the middle, one extreme can be considered better than the other extreme. In a further use case, the poor alternative may be denoted with shades of red, and the good alternative may be denoted with green (e.g., where green represents one extreme, and red represents an opposite directional degree). Because it is easy to distinguish variations in color with darker shades representing the higher magnitudes, such symbol color is an effective way to represent differences in magnitude of a phenomenon.

In some embodiments, system 10 comprises one or more computing devices 16, one or more processors 20, electronic storage 30, external resources 14, and/or other components. As shown in FIG. 1, system 10 may provide interfaces to and from external resources 14, electronic storage 30, or one or more other databases. Electronic storage 30 of FIG. 1 comprises electronic storage media that electronically stores information. The electronic storage media of electronic storage 30 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 30 may be (in whole or in part) a separate component within system 10, or electronic storage 30 may be provided (in whole or in part) integrally with one or more other components of system 10 (e.g., a computing device 16, processor 20, etc.).

In some embodiments, electronic storage 30 may be located in a server together with processor 20, in a server that is part of external resources 14, in computing devices 16, and/or in other locations. Electronic storage 30 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 30 may store software algorithms, information obtained and/or determined by processor 20, information received via computing devices 16 and/or other external computing systems, information received from external resources 14, and/or other information that enables system 10 to function as described herein.

External resources 14 include sources of information (e.g., databases, websites, etc.), external entities participating with system 10 (e.g., a medical records system that stores patient census information and a population records system that stores resident census information), one or more servers outside of system 10, a network (e.g., the Internet), electronic storage, equipment related to Wi-Fi technology, equipment related to Bluetooth® technology, data entry devices, and/or other resources. In some implementations, some or all of the functionality attributed herein to external resources 14 may be provided by resources included in system 10. External resources 14 may be configured to communicate with processor 20, computing device 16, electronic storage 30, and/or other components of system 10 via wired and/or wireless connections, via a network (e.g., a local area network and/or the Internet), via cellular technology, via Wi-Fi technology, and/or via other resources.

Computing device(s) 16 of system 10 may be configured to provide an interface between one or more users and system 10. Computing devices 16 are configured to provide information to and/or receive information from the one or more users. Computing devices 16 include a user interface and/or other components. The user interface may be and/or include a graphical user interface configured to present views and/or fields configured to receive entry and/or selection with respect to particular functionality of system 10, and/or provide and/or receive other information. In some embodiments, the user interface of computing devices 16 may include a plurality of separate interfaces associated with processors 20 and/or other components of system 10.

In some embodiments, computing devices 16 are configured to provide a user interface, processing capabilities, databases, and/or electronic storage to system 10. As such, computing devices 16 may include processors 20, electronic storage 30, external resources 14, and/or other components of system 10. In some embodiments, computing devices 16 are connected to a network (e.g., the Internet). In some embodiments, computing devices 16 do not include processor 20, electronic storage 30, external resources 14, and/or other components of system 10, but instead communicate with these components via dedicated lines, a bus, a switch, network, or other communication means. The communication may be wireless or wired. In some embodiments, computing devices 16 are laptops, desktop computers, smartphones, tablet computers, and/or other user interface devices.

Examples of interface devices suitable for inclusion in computing device 16 include a touch screen, a keypad, touch sensitive and/or physical buttons, switches, a keyboard, knobs, levers, a display, speakers, a microphone, an indicator light, an audible alarm, a printer, and/or other interface devices. The present disclosure also contemplates that computing devices 16 include a removable storage interface. In this example, information may be loaded into computing devices 16 from removable storage (e.g., a smart card, a flash drive, a removable disk) that enables users to customize the implementation of computing devices 16.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., a server), or processor 20 may represent processing functionality of a plurality of devices operating in coordination (e.g., one or more servers, computing devices 16, devices that are part of external resources 14, electronic storage 30, and/or other devices).

In some embodiments, processor 20, external resources 14, computing devices 16, electronic storage 30, and/or other components may be operatively linked via one or more electronic communication links. For example, such electronic communication links may be established, at least in part, via a network such as the Internet, and/or other networks. It will be appreciated that this is not intended to be limiting, and that the scope of this disclosure includes embodiments in which these components may be operatively linked via some other communication media. In some embodiments, processor 20 is configured to communicate with external resources 14, computing devices 16, electronic storage 30, and/or other components according to a client/server architecture, a peer-to-peer architecture, and/or other architectures.

As shown in FIG. 1, processor 20 is configured via machine-readable instructions to execute one or more computer program components. The computer program components may comprise one or more of presentation subsystem 22, test subsystem 24, monitoring subsystem 26, storage subsystem 28, or other components. Processor 20 may be configured to execute subsystems 22-28 by software; hardware; firmware; some combination of software, hardware, and/or firmware; and/or other mechanisms for configuring processing capabilities on processor 20.

It should be appreciated that although subsystems 22-28 are illustrated in FIG. 1 as being co-located within a single processing unit, in embodiments in which processor 20 comprises multiple processing units, one or more of subsystems 22-28 may be located remotely from the other components. The description of the functionality provided by the different subsystems 22-28 described below is for illustrative purposes, and is not intended to be limiting, as any of subsystems 22-28 may provide more or less functionality than is described. For example, one or more of subsystems 22-28 may be eliminated, and some or all of its functionality may be provided by other subsystems 22-28. As another example, processor 20 may be configured to execute one or more additional components that may perform some or all of the functionality attributed below to one of subsystems 22-28.

Figure 3:
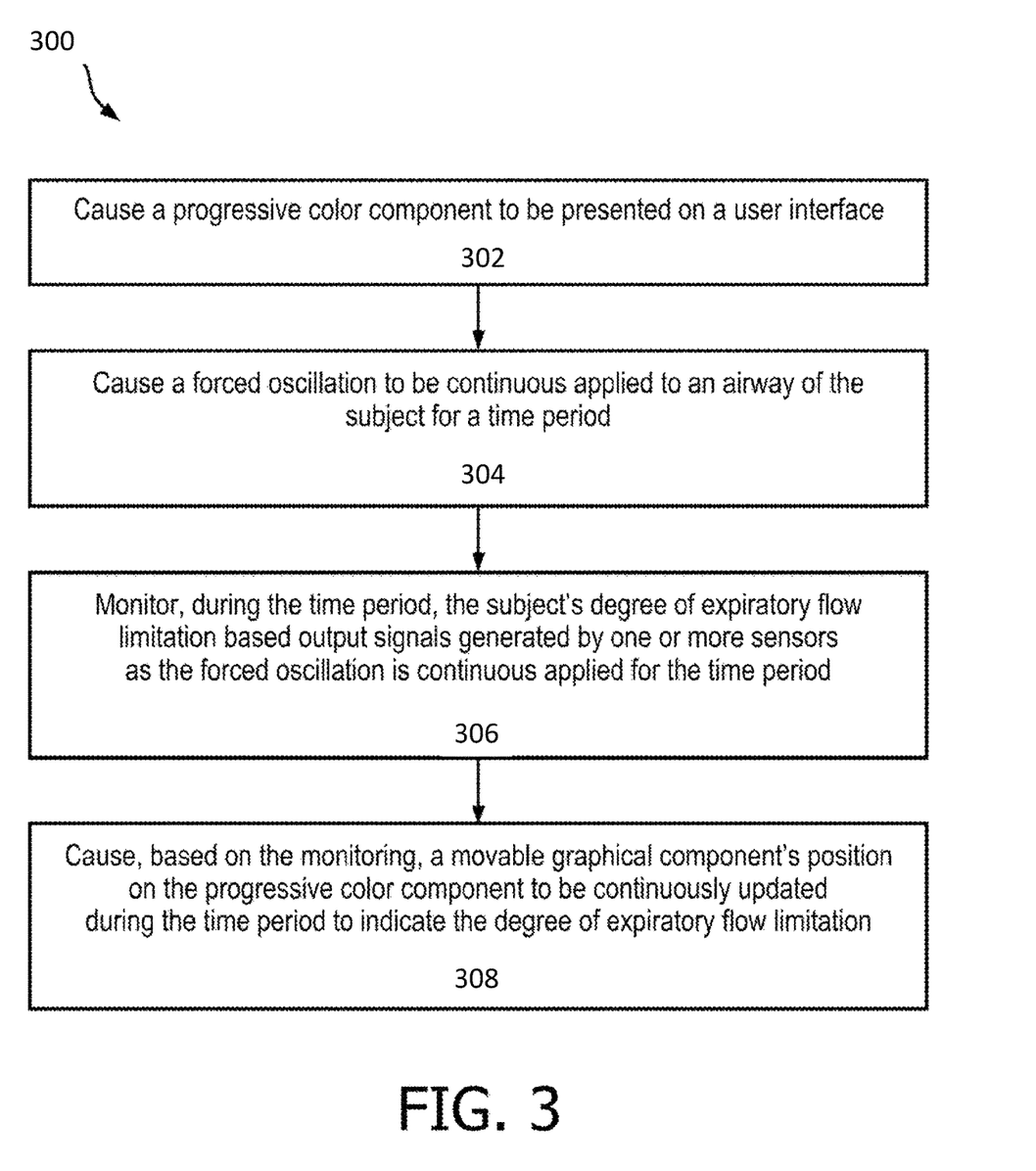
FIG. 3 illustrates a method for providing interactive guidance related to a subject's expiratory flow limitation results, in accordance with one or more embodiments.

FIG. 3 illustrates method 300 for providing interactive guidance related to a subject's expiratory flow limitation results, in accordance with one or more embodiments. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At operation 302, a progressive color component may be presented on a user interface. Such "colors" of the progressive color component may include only grayscale values or include one or more values other than grayscale values (in addition to or in lieu of grayscale values). As an example, the progressive color component may indicate a progression from one color proximate one side of the progressive color component to another color proximate another side of the progressive color component. As another example, the progressive color component may include a choropleth map, a component having a continuous color scheme that is used to apply different shades of the same color (e.g., such that lighter shades match lower data values and darker shades match higher data values), or other component. In some embodiments, operation 302 is performed by a processor component the same as or similar to presentation subsystem 22 (shown in FIG. 1 and described herein).

At operation 304, a forced oscillation may be caused to be continuously applied to an airway of the subject for a time period. As an example, the force oscillation may be provided via a moving valve, modulated motor, an adjustment of a blower inlet gap, or other source. As another example, the continuous application of the forced oscillation may include application of the forced oscillation on a periodic basis. In some embodiments, operation 304 is performed by a processor component the same as or similar to test subsystem 24 (shown in FIG. 1 and described herein).

At operation 306, the subject's degree of expiratory flow limitation may be monitor during the time period based on output signals (e.g., generated by one or more sensors) as the forced oscillation is continuously applied for the time period. As an example, the monitoring may include one or more of: continuously measuring, based on the sensor-generated output signals, reactance related to the subject's inspiration of gas during the time period and reactance related to the subject's expiration of gas during the time period as the forced oscillation is continuously applied for the time period; and determining and updating the subject's degree of expiratory flow limitation during the time period based on differences between the continuous measurements of the reactance related to the subject's inspiration of gas and the continuous measurements of reactance related to the subject's expiration of gas. In some embodiments, operation 306 is performed by a processor component the same as or similar to monitoring subsystem 26 (shown in FIG. 1 and described herein).

At operation 308, a movable graphical component's position on the progressive color component may be continuously updated during the time period based on the monitoring to indicate the subject's degree of expiratory flow limitation. As an example, the continuous updating may include periodically updating, during the time period, the movable graphical component's position on the progressive color component based on the monitoring to indicate the subject's degree of expiratory flow limitation. In some embodiments, operation 308 is performed by a processor component the same as or similar to storage subsystem 26 (shown in FIG. 1 and described herein).

Figure 4:
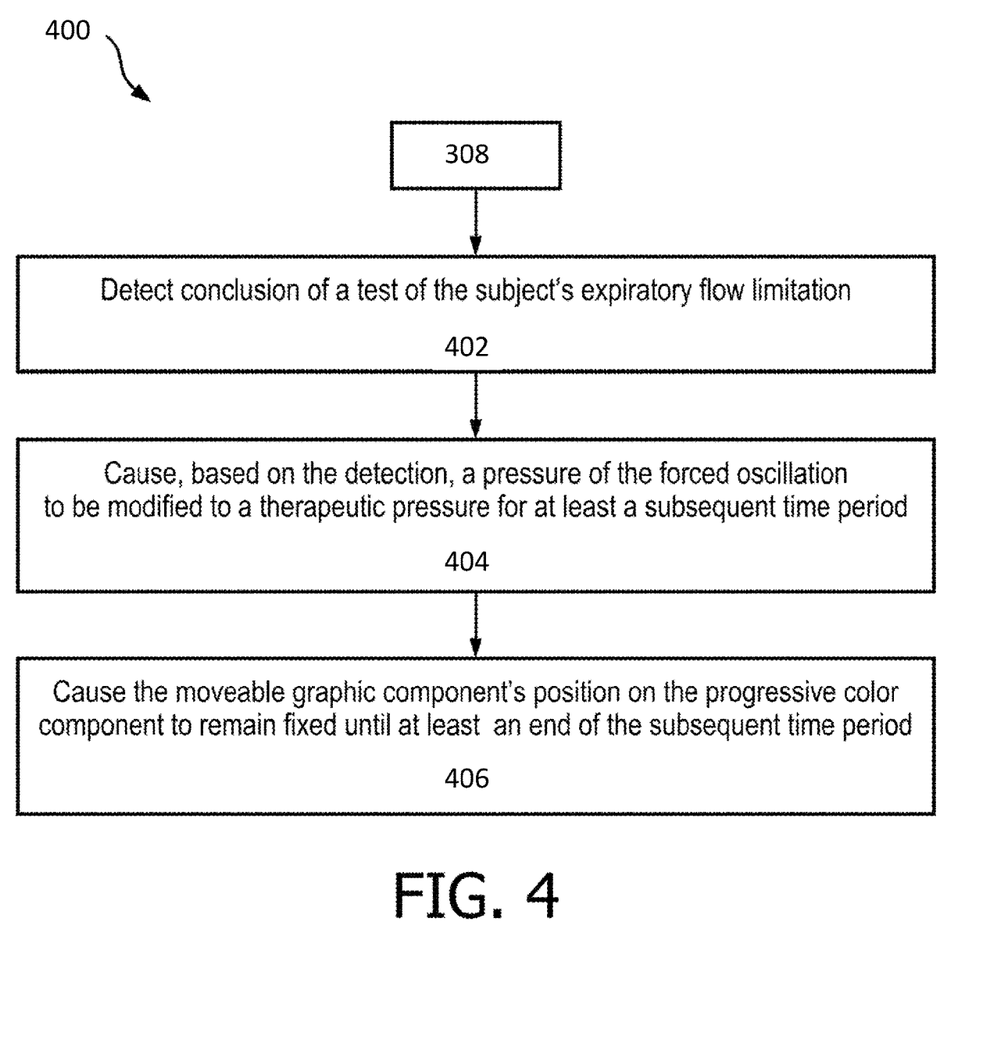
FIG. 4 illustrates a method for facilitating subsequent test actions following a test of a subject's expiratory flow limitation, in accordance with one or more embodiments.

FIG. 4 illustrates method 400 for providing interactive guidance related to a subject's expiratory flow limitation results, in accordance with one or more embodiments. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At operation 402, conclusion of a test of the subject's expiratory flow limitation may be detected. As an example, the time period may be a fixed time period, and the conclusion of the test may be detected responsive to the occurrence of the end of the fixed time period (e.g., based on a timer or other indication). As another example, the conclusion of the test may be detected responsive to finalization of the subject's degree of expiratory flow limitation. In one use case, the finalization of the subject's degree of expiratory flow limitation may be detected based on one or more degree change thresholds (e.g., if the calculated degree has not changed by more than a first degree threshold for at least a first threshold number of updates or amount of time, if the calculated degree has not changed by more than a second degree threshold value for at least a second threshold number of updates or amount of time, etc.). In some embodiments, operation 402 is performed by a processor component the same as or similar to monitoring subsystem 26 (shown in FIG. 1 and described herein).

At operation 404, a pressure of the forced oscillation may be modified to a therapeutic pressure for at least a subsequent time period based on the detection of the test conclusion. As an example, where the pressure of the forced oscillation is about 3 cmH2O during an expiratory flow limitation test, the pressure may be increased from 3 cmH2O to about 4 cmH2O or other therapeutic pressure (e.g., between about 4 cmH20 to about 10 cmH20, between about 4 cmH20 to about 15 cmH20, between about 4 cmH20 to about 20 cmH20, etc.). In some embodiments, operation 404 is performed by a processor component the same as or similar to test subsystem 24 (shown in FIG. 1 and described herein).

At operation 406, the moveable graphical component's position on the progressive color component may be caused to remain fixed until at least an end of the subsequent time period. In some embodiments, operation 406 is performed by a processor component the same as or similar to presentation subsystem 22 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment. The present techniques will be better understood with reference to the following enumerated embodiments:

1. A method comprising: causing a progressive color component to be presented on a user interface, the progressive color component indicating a progression from one color proximate one side of the progressive color component to another color proximate another side of the progressive color component; causing a forced oscillation to be continuously applied to an airway of the subject for a time period; monitoring, during the time period, the subject's degree of expiratory flow limitation based output signals generated by one or more sensors as the forced oscillation is continuously applied for the time period; and causing, based on the monitoring, a movable graphical component's position on the progressive color component to be continuously updated during the time period to indicate the subject's degree of expiratory flow limitation.

2. The method of embodiment 1, wherein the progressive color component includes one or more values other than grayscale values.

3. The method of embodiment 1, wherein the progressive color component includes only grayscale values.

4. The method of any of embodiments 1-3, wherein continuously updating the movable graphical component's position on the progressive color component comprises periodically updating, during the time period, the movable graphical component's position on the progressive color component based on the monitoring to indicate the subject's degree of expiratory flow limitation.

5. The method of any of embodiments 1-4, wherein monitoring the subject's degree of expiratory flow limitation comprises: continuously measuring, based on the sensor-generated output signals, reactance related to the subject's inspiration of gas during the time period and reactance related to the subject's expiration of gas during the time period as the forced oscillation is continuously applied for the time period; and determining and updating the subject's degree of expiratory flow limitation during the time period based on differences between the continuous measurements of the reactance related to the subject's inspiration of gas and the continuous measurements of reactance related to the subject's expiration of gas, wherein the movable graphical component's position on the progressive color component to be continuously updated during the time period to reflect the subject's updated degree of expiratory flow limitation.

6. The method of any of embodiments 1-5, further comprising: detecting conclusion of a test of the subject's expiratory flow limitation; causing, based on the detection of the test conclusion, a pressure of the forced oscillation to be modified to a therapeutic pressure for at least a subsequent time period; and causing the moveable graphical component's position on the progressive color component to remain fixed until at least an end of the subsequent time period.

7. The method of any of embodiments 1-6, further comprising: detecting finalization of the subject's degree of expiratory flow limitation based on one or more degree change thresholds; causing, based on the finalization detection, a pressure of the forced oscillation to be modified to a therapeutic pressure for at least a subsequent time period; and causing the moveable graphical component's position on the progressive color component to remain fixed until at least an end of the subsequent time period.

8. A tangible, non-transitory, machine-readable medium storing instructions that when executed by a data processing apparatus cause the data processing apparatus to perform operations comprising those of any of embodiments 1-7.

D1. A ventilator comprising: one or more sensors; one or more processors; and memory storing instructions that, when executed by the processors, cause the processors to effectuate operations comprising those of any of embodiments 1-7.

E1. A system comprising: one or more sensors; one or more processors; and memory storing instructions that when executed by the processors cause the processors to effectuate operations comprising those of any of embodiments 1-7.

What is claimed is:

1. A ventilator configured to providing interactive guidance related to a subject's expiratory flow limitation results, the ventilator comprising:
one or more sensors configured to be placed at or near a subject's mouth and to generate output signals conveying information related to the subject's inspiration or expiration of gas; and
one or more physical processors configured by machine readable instructions to:
cause a progressive color component to be presented on a user interface, the progressive color component indicating a progression from one color proximate one side of the progressive color component to another color proximate another side of the progressive color component;
cause, via an oscillator, a forced oscillation to be continuously applied to an airway of the subject for a test period;
monitor, during the test period, the subject's degree of expiratory flow limitation based on the sensor-generated output signals as the forced oscillation is continuously applied for the test period;
cause, based on the monitoring, a movable graphical component's position on the progressive color component to be updated to indicate the subject's degree of expiratory flow limitation;
detect finalization of the subject's degree of expiratory flow limitation based on one or more degree change thresholds;
cause, based on the finalization detection, a pressure of the forced oscillation to be modified to a therapeutic pressure for at least a subsequent time period; and
cause the moveable graphical component's position on the progressive color component to remain fixed until at least an end of the subsequent time period.

2. The ventilator of claim 1, wherein the progressive color component includes one or more values other than grayscale values.

3. The ventilator of claim 1, wherein the progressive color component includes only grayscale values.

4. The ventilator of claim 1, wherein continuously updating the movable graphical component's position on the progressive color component comprises periodically updating, during the test period, the movable graphical component's position on the progressive color component based on the monitoring to indicate the subject's degree of expiratory flow limitation.

5. The ventilator of claim 1; wherein monitoring the subject's degree of expiratory flow limitation comprises:
continuously measuring, based on the sensor-generated output signals, reactance related to the subject's inspiration of gas during the test period and reactance related to the subject's expiration of gas during the test period as the forced oscillation is continuously applied for the test period; and
determining and updating the subject's degree of expiratory flow limitation during the test period based on differences between the continuous measurements of the reactance related to the subject's inspiration of gas and the continuous measurements of reactance related to the subject's expiration of gas, wherein the movable graphical component's position on the progressive color component to be continuously updated during the test period to reflect the subject's updated degree of expiratory flow limitation.

6. A method of providing interactive guidance related to a subject's expiratory flow limitation results, the method being implemented by a computer system comprising one or more physical processors, the method comprising:
causing a progressive color component to be presented on a user interface, the progressive color component indicating a progression from one color proximate one side of the progressive color component to another color proximate another side of the progressive color component;
causing a forced oscillation to be continuously applied to an airway of the subject for a test period;
monitoring, during the test period, the subject's degree of expiratory flow limitation based output signals generated by one or more sensors as the forced oscillation is continuously applied for the test period;
causing, based on the monitoring, a movable graphical component's position on the progressive color component to be updated to indicate the subject's degree of expiratory flow limitation;
detecting finalization of the subject's degree of expiratory flow limitation based on one or more degree change thresholds;
causing, based on the finalization detection, a pressure of the forced oscillation to be modified to a therapeutic pressure for at least a subsequent time period; and
causing the moveable graphical component's position on the progressive color component to remain fixed until at least an end of the subsequent time period.

7. The method of claim 6, wherein the progressive color component includes one or more values other than grayscale values.

8. The method of claim 6, wherein the progressive color component includes only grayscale values.

9. The method of claim 6, wherein continuously updating the movable graphical component's position on the progressive color component comprises periodically updating, during the test period, the movable graphical component's position on the progressive color component based on the monitoring to indicate the subject's degree of expiratory flow limitation.

10. The method of claim 6, wherein monitoring the subject's degree of expiratory flow limitation comprises:
continuously measuring, based on the sensor-generated output signals, reactance related to the subject's inspiration of gas during the test period and reactance related to the subject's expiration of gas during the test period as the forced oscillation is continuous applied for the test period; and
determining and updating the subject's degree of expiratory flow limitation during the period based on differences between the continuous measurements of the reactance related to the subject's inspiration of gas and the continuous measurements of reactance related to the subject's expiration of gas, wherein the movable graphical component's position on the progressive color component to be continuously updated during the test period to reflect the subject's updated degree of expiratory flow limitation.

11. A system for providing interactive guidance related to a subject's expiratory flow limitation results, the system comprising:
means for causing a progressive color component to be presented on a user interface, the progressive color component indicating a progression from one color proximate one side of the progressive color component to another color proximate another side of the progressive color component;
means for causing a forced oscillation to be continuously applied to an airway of the subject for a test period;
means for monitoring, during the test period, the subject's degree of expiratory flow limitation based on output signals generated by one or more sensors as the forced oscillation is continuously applied for the test period;
means for causing, based on the monitoring, a movable graphical component's position on the progressive color component to be updated to indicate the subject's degree of expiratory flow limitation;
means for detecting finalization of the subject's degree of expiratory flow limitation based on one or more degree change thresholds;
means for causing, based on the finalization detection, a pressure of the forced oscillation to be modified to a therapeutic pressure for at least a subsequent time period;
and means for causing the moveable graphical component's position on the progressive color component to remain fixed until at least an end of the subsequent time period.

12. The system of claim 11, wherein the progressive color component includes one or more values other than grayscale values.

13. The system of claim 11, wherein continuously updating the movable graphical component's position on the progressive color component comprises periodically updating, during the test period, the movable graphical component's position on the progressive color component based on the monitoring to indicate the subject's degree of expiratory flow limitation.

14. The system of claim 11, wherein monitoring the subject's degree of expiratory flow limitation comprises:
continuously measuring, based on the sensor-generated output signals, reactance related to the subject's inspiration of gas during the test period and reactance related to the subject's expiration of gas during the test period as the forced oscillation is continuously applied for the test period; and
determining and updating the subject's degree of expiratory flow limitation during the test period based on differences between the continuous measurements of the reactance related to the subject's inspiration of gas and the continuous measurements of reactance related to the subject's expiration of gas, wherein the movable graphical component's position on the progressive color component to be continuously updated during the test period to reflect the subject's updated degree of expiratory flow limitation.

\* \* \* \* \*